(12) United States Patent
Bardorz et al.

(10) Patent No.: US 12,064,539 B2
(45) Date of Patent: Aug. 20, 2024

(54) MEDICAL DEVICE

(71) Applicant: Fresenius Medical Care Deutschland GmbH, Bad Homburg (DE)

(72) Inventors: Christoph Bardorz, Rottendorf (DE); Jochen Siebert, Strahlungen (DE); Stefan Kellermann, Massbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1003 days.

(21) Appl. No.: 16/982,703

(22) PCT Filed: Mar. 22, 2019

(86) PCT No.: PCT/EP2019/057283
§ 371 (c)(1),
(2) Date: Sep. 21, 2020

(87) PCT Pub. No.: WO2019/180228
PCT Pub. Date: Sep. 26, 2019

(65) Prior Publication Data
US 2021/0001028 A1    Jan. 7, 2021

(30) Foreign Application Priority Data

Mar. 22, 2018 (DE) .......................... 102018106906.5

(51) Int. Cl.
*A61M 1/16* (2006.01)
(52) U.S. Cl.
CPC ....... *A61M 1/1601* (2014.02); *A61M 2205/16* (2013.01); *A61M 2205/52* (2013.01); *A61M 2205/70* (2013.01)
(58) Field of Classification Search
CPC .......... A61M 2205/16; A61M 2205/52; A61M 2205/70; A61M 2205/17; A61M 1/1601; A61M 1/14
See application file for complete search history.

(56) References Cited

U.S. PATENT DOCUMENTS

| 5,226,152 A | 7/1993 | Klug et al. |
| 6,170,044 B1 | 1/2001 | McLaughlin et al. |
| (Continued) | | |

FOREIGN PATENT DOCUMENTS

| DE | 4131247 | 4/1993 |
| EP | 0518630 | 12/1992 |
| (Continued) | | |

OTHER PUBLICATIONS

PCT International Preliminary Report on Patentability in International Appln. No. PCT/EP2019/057283, mailed Oct. 1, 2020, 16 pages (with English translation).

(Continued)

*Primary Examiner* — Michael J Tsai
*Assistant Examiner* — Rachel T. Smith
(74) *Attorney, Agent, or Firm* — Fish & Richardson P.C.

(57) ABSTRACT

The present disclosure pertains to medical device such as a dialysis device for performing a hemodialysis, and/or hemofiltration and/or hemodiafiltration. The medical device can include a first functional module and a second functional module, wherein an operating hours counter for counting the operating hours is provided in the first functional module, and wherein the first functional module is configured to store an operating hours value determined by the operating hours counter in a first storage of the first functional module. In some embodiments, a second storage is provided in the second functional module, wherein the second functional module is configured to store the operating hours value determined by the operating hours counter of the first functional module in the second storage.

20 Claims, 1 Drawing Sheet

(56) References Cited

U.S. PATENT DOCUMENTS

| | | | |
|---|---|---|---|
| 6,423,268 B1 * | 7/2002 | King | A61M 1/3664 210/260 |
| 7,873,489 B2 | 1/2011 | Dolgos et al. | |
| 2002/0104004 A1 | 8/2002 | Couillard | |
| 2013/0190674 A1 * | 7/2013 | Case | G16H 40/67 604/6.01 |
| 2017/0238251 A1 * | 8/2017 | Lu | H04W 52/0216 370/311 |

FOREIGN PATENT DOCUMENTS

| | | |
|---|---|---|
| EP | 1698361 | 9/2006 |
| JP | 2009171053 A * | 7/2009 |

OTHER PUBLICATIONS

PCT International Search Report and Written Opinion in International Appln. No. PCT/EP2019/057283, mailed Jun. 25, 2019, 19 pages (with English translation).

* cited by examiner

MEDICAL DEVICE

CROSS-REFERENCE TO RELATED APPLICATIONS

The present application is the national stage entry of International Patent Application No. PCT/EP2019/057283, filed on Mar. 22, 2019, and claims priority to Application No. DE 10 2018 106 906.5, filed on Mar. 22, 2018, the disclosures of which are expressly incorporated herein in their entirety by reference thereto.

TECHNICAL FIELD

The present invention relates to a medical device for performing a treatment on a patient, preferably a dialysis device, by which, for example, a hemodialysis, a hemofiltration or a hemodiafiltration may be performed.

TECHNOLOGICAL BACKGROUND

In medical devices it is of importance that the integrity and the safety of the medical device is ensured at any time during operation. For this purpose, safety measures are provided within the medical device, by which the medical device monitors itself during the treatment. In this way, a failure safety may also be provided and corresponding measurements may be taken in the event of a failure, for example, outputting an error message, triggering an alarm, and/or stopping or terminating the treatment to ensure the safety of the patient at any time.

SUMMARY OF THE INVENTION

Redundant control mechanisms are provided in some medical devices as described herein, for example dialysis devices, wherein e.g. a main control module is provided, which controls the dialysis device in operation and during the treatment. Furthermore, a protection module is provided, which operates independently of the main control module and by which the main control module is monitored. The protection module may, for example, be provided in the form of a second module, which is built or designed essentially identical to the main control module and may intervene in case of damage of the main control module and may bring the medical device in a safe state. Aside from the mentioned main control modules and protection modules additional functional modules may be provided in medical devices, which also operate independently of the main control module and may, for example, be provided in the form of a display module or monitoring module. Single functional components and functional subgroups of the medical device may also be operated with functional modules, which act independently of the main control module. The different functional modules commonly communicate with each other via a bus and/or defined interfaces.

Aside from the monitoring of the function of the medical device during operation prior to the respective treatment of the patient, during the treatment of the patient, and after the treatment of the patient, as well as during routine test and maintenance sequences, an operating hours counter is provided as a further device and/or safety mechanism of the medical device. With said operating hours counter the total operating time of the medical device or the operating time of single components may be determined. Accordingly, maintenance of specific components or of the entire medical device may be performed after expiry of a predetermined operating time to further ensure the safe functioning of the medical device.

After expiry of a predefined operating time of single components a replacement of the respective components may also be necessary. By means of documentation and displaying of the expired operation time an incentive for maintenance may be provided or a replacement of components may be initiated. The documentation of the operation time is superior to the mere indication of, for example, a production date or an expiry date, since this allows the determining of the actual use of the medical device and a maintenance or replacement need may be derived from the corresponding wear due to operation. Said maintenance or replacement need, however, is not necessarily derivable from a fixed predefined date, which may lead to a situation, wherein the maintenance need decider retrieved too early, such that the wear of the components does not correspond to the actual use of the medical device and maintenance accordingly is uneconomical, or wherein the maintenance need is retrieved too late, such that with a heavy use of the medical device the safety of the medical device may potentially be jeopardized, since the aware of the components has already progressed too much. Accordingly, a documentation of the actual operating hours is preferred for economic reasons and for reasons of operation safety.

The operating hours may be counted by means of a mechanical counter in the medical device, although a mechanical operating hours counter is associated with additional costs and the mechanical operating hours counter, as a mechanical component, is subject to wear and hence a limited operation safety.

Furthermore, operating hours counters are disclosed herein which are electronically implemented in a main control module or on the main printed circuit board of the medical device. Accordingly, a microcontroller uses the processor frequency, counts the operating hours based thereupon, and stores the determined operating hours value in a non-transitory storage medium in the main control module. However, in case of a defect of the non-transitory storage medium or of the main control module or in case of an exchange or replacement of the main control module or the main printed circuit board, the operating hours counter accordingly becomes invalid and must be reset by a service person in a cumbersome manner.

In a further implementation, as present in, for example, the dialysis devices 5008/6008 of the applicant, some of the functional modules, in particular a main control module, a protection module, and a monitoring module, are each equipped with an individual operating hours counter, which count the operating time of the respective functional module based on the processor frequency of the processor of the respective functional module independent from each other. After switching on the machine, the operating hours counters of the functional modules are compared to each other and synchronized with each other, when a deviation between the individual values is smaller than one hour. However, when the deviation is larger, a failure message is outputted. In this case, the problem also occurs that by default a failure message is outputted, when a module is replaced, since the operating hours counter of the newly inserted module inevitably deviates from the values of the operating hours counters of the remaining modules. Accordingly, a cumbersome comparison of the operating hours counters must also be performed by a service person after a module replacement.

Some embodiments described herein provide a medical device which provides a robust operating hours counter, which simplifies the maintenance of the medical device.

Accordingly, a medical device is described herein, preferably a dialysis device for performing a hemodialysis and/or hemofiltration and/or hemodiafiltration, comprising a first functional module and a second functional module, wherein an operating hours counter for counting the operating hours is provided in the first functional module, and wherein the first functional module is configured to store an operating hours value determined by the operating hours counter in the a first storage of the first functional module, wherein a second storage is provided in the second functional module. According to the disclosure, the second functional module is configured to store the operating hours value determined by the operating hours counter of the first functional module in the second storage.

Since a second storage is provided in the second functional module, which is configured to store the operating hours value determined by the operating hours counter of the first functional module, the operating hours value as determined by the operating hours counter is recorded in at least two different storages in two different functional modules. Such a redundant storage of the operating hours value determined by an operating hours counter leads to a robust operating hours counter, such that also in cases of maintenance and/or during replacement of a functional module the operating hours value as originally determined in the medical device remains in the medical device.

Furthermore, and asynchronous incrementing of the same operating hours by different operating hours counters in different modules no longer occurs, thereby omitting the necessity of a synchronization in normal operation.

Furthermore, the operating hours value determined by the operating hours counter of the first functional module is accordingly stored in at least one further functional model directly in a storage, such that the counter value determined by the central operating hours counter is redundantly stored, but not determined by multiple modules. As a result, a synchronization between the operating hours values present in the different storages of the different functional modules is present in normal operation, since they have only been determined by a single operating hours counter.

During replacement of a functional module the operating hours value recorded in a storage of another functional module may be accessed and said operating hours value then forms a basis for the actual operating hours value. The medical device accordingly assumes that every operating hours value recorded in the medical device in a storage corresponds to the actual run time or actually lapsed operating hours of the medical device. Accordingly, a plausibility test is at first not necessary.

As such, it may be avoided for those typical situations, wherein the replacement of a functional module is necessary, that a technician elaborately has to reset an operating hours counter, which has become invalid. Rather, it may be referred to the operating hours value stored in another functional module.

In other words, it is facilitated in this way that the operating hours value determined by the operating hours counter is recorded in different positions or in different functional modules within the medical device, such that due to the provision of such "backups" during the replacements of one or more functional modules, it may still be relied upon, or referred to a valid operating hours value of the operating hours counter, which is then preferably automatically adopted by the newly inserted functional module.

Preferably, the first functional module is a main control module and/or an operating system and/or the second functional module (CPU2) is a monitoring system and/or a protection system. More preferably, the first functional module and the second functional model each comprise an individual microprocessor. In other words, the individual functional modules are to a certain extent autonomous and preferably comprise an own or individual microprocessor and an own storage. In a further embodiment, however, also only a storage and no microprocessor may be arranged at some of the functional modules, such that the storage of the operating hours value in the storage may be achieved in this functional module also without the requirement of a microprocessor.

Preferably, at least two further functional modules are provided in addition to the first functional module, which each comprise an individual storage, wherein the further functional modules are each configured to store the operating hours value determined by the operating hours counter of the first functional module in the respective storage, and wherein particularly preferred each functional module comprises an individual microprocessor.

Since multiple functional modules are provided, wherein the operating hours value are stored, an even higher redundancy as to the storage of the operating hours value may be achieved, such that the robustness of the operating hours counter is even further increased. For example, during a failure or downtime or replacements of multiple functional modules, it may still be relied upon the operating hours value stored in the storage of a further functional module and as such, it may be referred to the actually elapsed operating hours in the medical device and also an automatic synchronization and/or resetting of the operating hours values that have become invalid may be carried out.

Preferably, a communication interface is provided between the first functional module and the second functional module, which is configured to transmit the operating hours value determined by the operating hours counter of the first functional module to the second storage, preferably to each storage of the further functional modules. With the communication interface it is furthermore possible to read out the operating hours value stored in a storage by another functional module to determine in a first functional module whether the operating hours value stored in a second functional module deviates from the value stored in the first functional module.

In a preferred embodiment, a synchronization device is provided, which is configured to automatically synchronize the operating hours values stored in the storages of the functional modules to each other and/or to automatically restore the operating hours values. It is particularly preferred that an automatic resetting of the operating hours values is performed, when a deviation of the values occurs after maintenance or replacement of a printed circuit board or a functional module. As such, a replacement of modules may be performed without any further workload regarding the operating hours counter. For example, the storage on the newly connected printed circuit board may then automatically be set according to the operating hours value stored in the remaining storage of the medical device.

In the synchronization device a majority decision is preferably made, when more than two storages with different operating hours values are present. The operating hours value that is hence indicated as false based upon said decision is automatically restored or recovered.

For safety reasons, the largest operating hours value may preferably also be recognized as the correct operating hours value and be accordingly adopted.

The storage provided in the first functional module and/or the storage provided in the second functional module and/or all functional modules is preferably adapted or formed as a non-transient storage medium.

Preferably, the first storage of the functional module is configured to store further values, optionally configuration values and/or set up values and/or calibration values, wherein the second functional module is configured to store the further values stored in the storage of the first functional module in the second storage, and wherein optionally the synchronization device is configured to automatically synchronize the further values stored in the storages of the functional modules to each other and/or to automatically restore said values.

Accordingly, also for further values of the medical device, for example, configuration values and/or set of values and/or calibration values, a redundant storage of said values in the medical device may be provided, such that, for example, during replacement of a functional module, an automatic synchronization of said values may be carried out. Therefore, it may be achieved that the medical device is essentially in the same configuration status after the replacement of a functional module compared with the situation prior to the replacement of the functional module. Hence, a user of the medical device may continue the use of the medical device directly after the replacement of the functional module and does not need to perform an elaborate new configuration.

This disclosure also describes a method for accounting the operating hours of a medical device, preferably a dialysis device for performing a hemodialysis and/or hemofiltration and/or hemodiafiltration, which comprises a first functional module and a second functional module, wherein the first functional module determines the operating hours with an operating hours counter and wherein the determined operating hours value is stored in a storage of the first functional module. According to the disclosure, the operating hours value determined by the operating hours counter of the first functional module is stored in a second storage comprised by the second functional module.

Since the operating hours value determined by the operating hours counter of the first functional module is also stored in at least a second functional module, a synchronization of the operating hours values stored redundantly, i.e. essentially as backups, in the different functional modules is ensured on the one hand, while on the other hand, a simple synchronization and/or a simple restoring of the correct operating hours value from one or more operating hours values stored in the storages may be achieved, when a deviation occurs. Accordingly, a simple replacement of functional modules may be performed without losing the values of the operating hours counters and without additional effort of maintenance personnel.

Preferably, the operating hours value determined by the operating hours counter of the first functional module is stored in further storages of further functional modules, such that an even higher redundancy is achieved.

According to an advantageous embodiment of the method, an automatic synchronization and/or restoring of the operating hours values is performed, when a deviation of the operating hours values stored in the storages exists. Accordingly, a restoring of the operating hours value determined by the operating hours counter may be achieved without further effort of the servicing technician, for example during a replacement of the functional module, such that a particular robust and efficient method for counting of the operating hours of a medical device may be provided.

Furthermore, the automatic synchronization and/or restoring of the operating hours values may be performed after a user input and/or after maintenance and/or switching on of the medical device and/or according to schedule.

An automatic synchronization and/or restoring of the operating hours values may also be performed, when a predefined minimal deviation of the operating hours values stored in the storages exists to achieve a synchronization of the operating hours values stored in the medical device.

Advantageously, the operating hours value which is most frequently present in the storages is used as a basis for the synchronization and/or restoring of the operating hours values. Hence, essentially a majority decision is made and based on said decision it is decided which of the recorded operating hours values is eventually considered to be determining or decisive.

Preferably, further values are stored in the first storage of the first functional module, optionally configuration values and/or set up values and/or calibration values, and the further values stored in the storage of the first functional module are stored in the second functional module in the second storage, and wherein optionally the further values stored in the storages of the functional modules are automatically synchronized to each other and/or are automatically restored.

BRIEF DESCRIPTION OF THE DRAWINGS

Preferred further embodiments of the disclosure will be more readily appreciated by reference to the following detailed description when being considered in connection with the accompanying drawings in which.

DETAILED DESCRIPTION OF PREFERRED EMBODIMENTS

Figure 1:
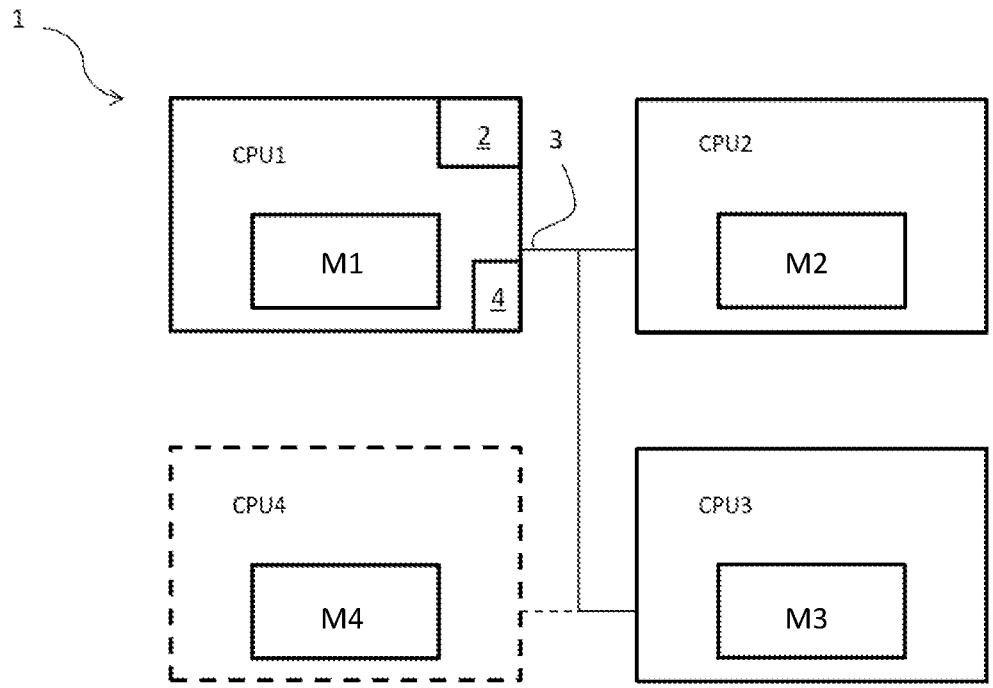
FIG. 1 is a schematic view of a medical device with multiple functional modules.

In the following, example embodiments will be explained with reference to the accompanying Figures. In the Figures, like elements are denoted by identical reference numerals and repeated description thereof may be omitted in order to avoid redundancies.

FIG. 1 schematically shows the composition or setup of a medical device 1, for example in form of a dialysis device for performing a hemodialysis and/or hemofiltration and/or hemodiafiltration.

In the medical device 1 a first functional module CPU1 is provided, which is, e.g., provided in the form of a main control module, which is responsible for the control of the medical device 1. With the first functional module CPU1 the treatment of the patient, for example, is controlled with the medical device.

The first functional module CPU1 comprises a microprocessor and a storage or memory M1. The storage M1 is preferably configured as a non-transitory storage medium to ensure a storage independently of the electrical supply of the functional module CPU1.

Furthermore, a second functional module CPU2 is provided in the medical device, which also comprises a microprocessor and a second non-transitory storage medium M2. The first functional module CPU1 and the second functional module CPU2 may be configured, for example, as a main control module or operating system on the one hand and as a protection system on the other hand. Both functional modules CPU1 and CPU2 may be configured redundantly with respect to each other, such that the protection system CPU2 may monitor the main control module CPU1. In case of a downtime of the main control system CPU1 the protection system CPU2 may intervene and may accordingly bring the medical device in a safe state and/or trigger an alarm and/or output a failure or error message.

Furthermore, a further functional module CPU3 is provided in the medical device 1, which may be adapted or formed as a monitoring system. Further functional modules may be provided—as indicated by the dashed lines in FIG. 1—for example in the form of the functional module CPU4, which may assume further functions within the medical device 1.

The functional modules CPU1, CPU2, CPU3, CPU4 each comprise an individual storage, M1, M2, M3, M4, preferably a non-transitory storage medium.

In the first functional module CPU1 an operating hours counter 2 is furthermore provided, by which the operating hours of the medical device 1 are counted and may be outputted as operating hours value. The operating hours counter 2 accordingly uses, for example, the processor frequency of the microprocessor in the first functional module CPU1 and accordingly increments the operating hours value after switching on the medical device 1. Alternatively, the treatment time or another time value, which should be measured during the operating time of the respective medical device 1, may be counted.

The operating hours value determined by the operating hours counter 2 in the first functional module CPU1 is stored or saved in the non-transitory storage M1 of the first functional module CPU1.

The storing may be performed, for example, every minute or in shorter or longer time intervals. The storing may also be exclusively or additionally performed upon the switching off of the device and/or at the start and/or completion of a treatment.

The operating hours value determined by the operating hours counter 2 provided in the first functional module CPU1 is furthermore communicated to e.g. the second functional module CPU2, the third functional module CPU3, and—depending on the implementation—also to the fourth functional module CPU4 and/or a further functional module via a communication interface 3 and is also stored in each of the respective storages M2 and M3 and—depending on the implementation—also in the optionally provided storage M4 and/or in the storages of optionally provided other functional modules. Accordingly, during normal operation and depending on the implementation a synchronization of the operating hours values exists in all storages M1, M2, M3, and optionally M4 of the respective functional modules CPU1, CPU2, CPU3, and optionally CPU4.

When replacement of a functional module is required, for example, the second functional module CPU2, an initialization is accordingly performed upon the insertion of the replacement functional module CPU2' and a comparison of the operating hours values recorded in the storages M1, M2', M3, and optionally M4 is performed.

In case of a replacement of the functional module it is determined that the operating hours value recorded in the storage M2' of the replaced functional module CPU2' does not correspond to the operating hours values that are recorded in the storages M1, M3, and optionally M4. Accordingly, the operating hours value present in the storage M2' of the replaced functional module CPU2' is restored by means of a synchronization device 4, which may be provided in the first functional module CPU1, based on the operating hours values recorded in the storages M1, M3, and optionally M4 of the other functional modules CPU1, CPU3, and optionally CPU4.

Accordingly, an automatic restoring and/or synchronization of the operating hours values occurs in all storages M1, M2', M3, and optionally M4 of the functional modules CPU1, CPU2', CPU3, and optionally CPU4, such that a synchronization of the operating hours values is provided. Hence, a comparison or a reset of the storage by a servicing technician does not need to be performed. Instead, an automatic comparison is provided.

If a deviation of the individual operating hours values in the respective storages M1, M2, M3, and optionally M4 is present, a majority decision, for example, is made by the synchronization device 4, when a deviation above a minimum is present, such that the operating hours value which is present in the largest number in the storages M1, M2, M3, and optionally M4, is given priority. Obviously, a majority decision may already be made when using three storages M1, M2, M3 and the additional optional storage M4 or the storage of further optional functional modules are not required for said decision, but may be considered in the decision, when present, although this is not necessary.

In case of a replacement of the functional module CPU2' this is accordingly the case in all functional modules CPU1, CPU3, and optionally CPU4, due to the synchronization of the operating hours values except for the newly inserted functional module CPU2'. Hence, an automatic restoring of the operating hours values in all storages M1, M2, M3, and optionally M3 may accordingly be achieved.

In this way, also a backup of the operating hours value, which is determined by the operating hours counter 2 in the first functional module CPU1, is accordingly achieved in the storages M2, M3, and optionally M4 of the other functional modules CPU2, CPU3, and optionally CPU4. Hence, a simple replacement of the functional modules is possible without losing the information regarding the elapsed operating time of the medical device 1.

In an exemplary embodiment, the operating hours value recorded in the first storage M1 is assumed to be valid for the restoring of the operating hours value, when a deviation smaller or equal to 5 hours between the individual operating hours values in the storages M2, M3, M4 and the first storage M1 of the first functional module CPU1 exist. The operating hours values in the storages M2, M3, and optionally M4 are set to the operating hours value derived from the first storage M1, if required.

In case of a deviation larger than 5 hours, a majority decision is made by recognizing which of the storages M1, M2, M3, and optionally M4 is defective and the wrong operating hours value is then automatically corrected. For safety reasons, the largest operating hours value of all operating hours values identified as being valid is taken.

The validity is determined as follows: If Wenn $|M1-M2| \leq 5$ h is true, the operating hours value in the storage M1 of the CPU1 and the operating hours value in the storage M2 of the CPU2 are identified as being valid. In general, the following comparisons need to be performed for each of the operating hours values stored in said storages:

$|M1-M2| \leq MAX\_DEV$
$|M1-M3| \leq MAX\_DEV$
$|M2-M3| \leq MAX\_DEV$

If no correction is possible (for example, because the deviation between all operating hours values is larger than 5 hours), a failure or error message is outputted.

Aside from the operating hours values also further values of the medical device may be redundantly stored or stored with a backup in the storages M1, M2, M3, and optionally M4 of the functional modules CPU1, CPU2, CPU3, and optionally CPU4. For example, configuration values and/or setup values and/or calibration values of the first functional module CPU1 may be stored in the storages M1, M2, M3, and optionally M4, and may be held synchronously by means of the synchronization device 4, such that, in case of a replacement of a functional module CPU1, CPU2, CPU3, and optionally CPU4, and in particular of the first functional module, it may be automatically relied upon the configuration values and/or setup values and/or calibration values.

Figure 2:
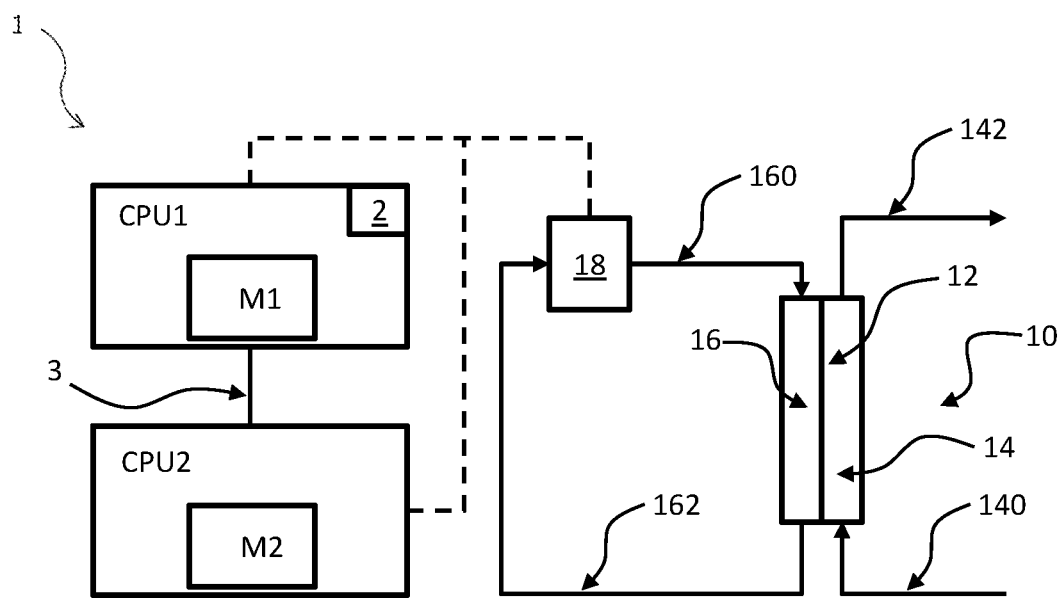
FIG. 2 is a schematic view of a dialysis device.

In FIG. 2 the medical device 1 is configured as a dialysis device according to a further embodiment. Accordingly, the device comprises a dialyzer 10, which comprises a blood space 14 and a dialysate space 16, wherein both spaces are separated from each other by means of a membrane 12. Dialyzers of this kind are generally known. They comprise a housing, wherein, for example, multiple cylindrically shaped hollow fiber membranes are adjoined into a hollow fiber bundle. Blood flows through the interior space of the hollow fiber membranes while dialysate flows in the space between the hollow fiber membranes and the filter housing. Obviously, other configurations of dialyzers may be provided.

Accordingly, the blood space 14 is to be understood as the sum of areas or regions, wherein blood flows in the dialyzer 10, and the dialysate space 16 is to be understood as the sum of the areas or regions, wherein dialysate flows. The wall of the membrane of the dialyzer 10 is configured as a semipermeable membrane, such that a mass exchange between the blood and the dialysate may occur. During hemodialysis, said exchange occurs by diffusion until a concentration balance is established between the blood space 14 and the dialysate space 16. Depending on the pore size of the membranes, larger or smaller molecules are allowed to pass into the dialysate space 16.

In operation, the dialysis device 1 is connected to a patient. The blood of the patient flows into the blood space 14 of the dialyzer 10 by means of a blood feed line 140 and is accordingly recirculated to the patient by means of the recirculation line 142. In the dialysate space 16 of the dialyzer 10 the dialysate preferably flows in counterflow direction with regard to the blood flow, as indicated by the arrows in FIG. 2. During the dialysis, the above described mass exchange between the blood and the dialysate occurs, wherein the latter subsequently exits the dialyzer 10 via the conduit or line 162. The dialysate hence includes the substances that have been removed from the blood circulation during the dialysis.

The dialysate is provided by a dialysate device 18. The dialysate device 18 facilitates that the dialysate flows into the dialysate space 16 via a dialysate line 160 and exits the dialysate space 16 via the dialysate line 162 and is recirculated to the dialysate device 18. The spent or used dialysate fed to the dialysate device 18 may be either separated from fresh dialysate and accordingly be disposed of or may at least partially be reused by a corresponding purification. It may also be provided that the dialysate is already disposed of upstream of the dialysate device 18.

To feed the dialysate in the accordingly formed dialysate circuit a dialysate pump (not shown) is provided, which, for example, may be arranged upstream or downstream of the dialyzer 10 or also in the dialysis device 18.

Accordingly, a blood pump for feeding the blood in the blood circuit of the dialyzer 10 is also provided (not shown). In addition, further dialysis components, such as valves, clamps, drip chambers, pressure measuring devices, or anticoagulation pumps, may be provided, which are, however, not shown in detail in the embodiment according to FIG. 2.

Also, two functional modules CPU1, CPU2 are arranged in the dialysis device 1, which essentially correspond to the functional modules according to FIG. 1.

The functional modules CPU1, CPU2 are connected to each other via a communication interface 3, such that the operating hours value, which is counted or determined by the operating hours counter 2 provided in the first functional module CPU1, is saved in the non-transitory storage medium M1 of the first functional module CPU1 and furthermore is transmitted to the second functional module CPU2 via a communication interface 3 and is saved in the corresponding storage M2 thereof. Accordingly, during normal operation and depending on the implementation, a synchronization of the operating hours values in all storages M1 and M2 of the respective functional module CPU1, CPU2 occurs.

Although not shown in further detail, further functional modules and/or a synchronization device may also be optionally provided, as described e.g. with respect to the embodiment of FIG. 1.

The first functional module CPU1 and the second functional module are depicted in FIG. 2 as separate functional modules, which are each communicatively connected to the dialysate device 18. Accordingly, it may be provided that the first functional module CPU1 is provided as a main control module or operating system, which assumes control of the medical device 1. Accordingly, the treatment of the patient with the medical device 1 is accordingly controlled with the first functional module CPU1. The second functional module CPU2 thereby fulfills the function of e.g. a protection system, which may monitor the main control module CPU1 and may bring the medical device 1 accordingly in a secure or safe state, in case of a downtime or defect of the main control system CPU1. The second functional module CPU2 may be configured to be redundant to the main control module. Although the functional modules CPU1, CPU2, as depicted in FIG. 2, are connected with the dialysate device 18, they may also be, alternatively, or in addition, connected to other components of the dialysis device 1 to accordingly control other functions of the dialysis treatment. For example, the functional modules may be connected to pumps and/or valves, which feed the blood or the dialysate in the respective circuit. Furthermore, the functional modules may be arranged in a separate device or may also be integrated in corresponding components, for example, as an integrated control device, wherein the operating hours value is stored in different storage media.

Where applicable, all of the respective features as depicted in the exemplary embodiments may be combined with each other and/or may be exchanged according to the scope of the disclosure.

LIST OF REFERENCE NUMERALS

1 Medical device
10 Dialyzer
12 Membrane
14 Blood space
140 Blood feed line

142 Recirculation line
16 Dialysate space
160 Dialysate line
162 Dialysate line
18 Dialysate device
2 Operating hours counter
3 Communication interface
4 Synchronization device
CPU1 First functional module
CPU2 Second functional module
CPU3 Third functional module
CPU4 Fourth, optional functional module
M1 First storage
M2 Second storage
M3 Third storage
M4 Fourth, optional storage

The invention claimed is:

1. A medical device for performing a hemodialysis and/or hemofiltration and/or hemodiafiltration, the medical device comprising:
 a first functional module; and
 a second functional module, wherein:
  the first functional module is a main control module;
  the second functional module is a monitoring system;
  the first functional module and the second functional module each comprise an individual microprocessor;
  an operating hours counter for counting operating hours of the medical device is provided in the first functional module,
  the first functional module is configured to store an operating hours value determined by the operating hours counter in a first storage of the first functional module,
  a second storage is provided in the second functional module, and
  the second functional module is configured to store the operating hours value determined by the operating hours counter of the first functional module in the second storage.

2. The medical device according to claim 1, wherein the first functional module is an operating system and the second functional module is a protection system.

3. The medical device according to claim 1, wherein the medical device comprises at least one further functional module, wherein the at least one further functional module comprises a respective storage, wherein the at least one further functional module is configured to store the operating hours value determined by the operating hours counter of the first functional module in the respective storage.

4. The medical device according to claim 3, wherein a communication interface is provided between the first functional module and the second functional module which is configured to transmit the operating hours value determined by the operating hours counter of the first functional module to the second storage.

5. The medical device according to claim 4, wherein the communication interface is also configured to transmit the operating hours value determined by the operating hours counter of the first functional module to respective storage of the at least one further functional module.

6. The medical device according to claim 3, wherein a synchronization device is provided, wherein the synchronization device is configured to automatically synchronize the operating hours values stored in the respective storages of the first functional module, the second functional module, and the at least one further functional module to each other and/or to automatically restore the operating hours values.

7. The medical device according to claim 3, wherein:
 the storage provided in the first functional module is a non-transient storage medium; and/or
 the storage provided in the second functional module is a non-transient storage medium; and/or
 the respective storage provided in the first functional module, the second functional module, and the at least one further functional module is a non-transient storage medium.

8. The medical device according to claim 3, wherein:
 the first storage of the first functional module is configured to store further values; and
 the second functional module is configured to store the further values stored in the first storage of the first functional module in the second storage.

9. The medical device according to claim 8, wherein the further values comprise configuration values, set up values, and/or calibration values.

10. The medical device according to claim 8, wherein a synchronization device is configured to automatically synchronize the further values stored in the respective storages of the first functional module, the second functional module, and the at least one further functional module to each other and/or to automatically restore said values.

11. The medical device according to claim 3, wherein each of the first function module, the second functional module, and the further functional module comprises an individual microprocessor.

12. A method for counting operating hours of a dialysis device for performing a hemodialysis and/or hemofiltration and/or hemodiafiltration, which comprises a first functional module and a second functional module, the method comprising:
 determining, by the first functional module, the operating hours of the dialysis device using an operating hours counter; and
 storing, in a first storage of the first functional module, the determined operating hours value,
 wherein:
  the first functional module is a main control module;
  the second functional module is a monitoring system;
  the first functional module and the second functional model each comprise an individual microprocessor; and
  the operating hours value determined using the operating hours counter of the first functional module is stored in a second storage comprised by the second functional module.

13. The method according to claim 12, wherein the operating hours value determined using the operating hours counter of the first functional module is stored in a respective further storage of at least one further functional module.

14. The method according to claim 13, wherein an automatic synchronization and/or restoring of the operating hours values is performed when a deviation exists between the operating hours values stored in the respective storages of the first functional module, the second functional module, and the at least one further functional module.

15. The method according to claim 14, wherein the automatic synchronization and/or restoring of the operating hours values is performed after a user input and/or after maintenance and/or switching on of the dialysis device and/or according to schedule.

16. The method according to claim 14, wherein the automatic synchronization and/or restoring of the operating hours values is performed when a predefined minimal deviation exists between the operating hours values stored in the respective storages of the first functional module, the second functional module, and the at least one further functional.

17. The method according to claim 14, wherein the operating hours value which is most frequently present in the respective storages of the first functional module, the second functional module, and the at least one further functional is used as a basis for the synchronization and/or restoring of the operating hours values.

18. The method according to claim 12, wherein further values are stored in the first storage of the first functional module and in the second storage of the second functional module.

19. The method according to claim 18, wherein the further values stored in the first storage are configuration values and/or set up values and/or calibration values.

20. The method according to claim 18, wherein the further values stored in the respective storages of the first functional module, the second functional module, and the at least one further functional module are automatically synchronized to each other and/or are automatically restored.

\* \* \* \* \*